(12) United States Patent
Nakamura

(10) Patent No.: US 9,060,736 B2
(45) Date of Patent: Jun. 23, 2015

(54) X-RAY IMAGING APPARATUS

(71) Applicant: CANON KABUSHIKI KAISHA, Tokyo (JP)

(72) Inventor: Takashi Nakamura, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 388 days.

(21) Appl. No.: 13/692,807

(22) Filed: Dec. 3, 2012

(65) Prior Publication Data

US 2013/0142307 A1 Jun. 6, 2013

(30) Foreign Application Priority Data

Dec. 5, 2011 (JP) ................................. 2011-265894

(51) Int. Cl.
*G01N 23/04* (2006.01)
*A61B 6/00* (2006.01)

(52) U.S. Cl.
CPC ................ *A61B 6/484* (2013.01); *G01N 23/04* (2013.01)

(58) Field of Classification Search
CPC ....................................................... A61B 6/484
USPC ........................ 378/62, 70, 82–85.91, 98.12
See application file for complete search history.

(56) References Cited

U.S. PATENT DOCUMENTS

| 2009/0316857 | A1   | 12/2009 | David et al. |
| 2010/0061508 | A1   | 3/2010  | Takahashi |
| 2011/0243300 | A1 * | 10/2011 | Kaneko et al. ................. 378/36 |
| 2011/0243302 | A1 * | 10/2011 | Murakoshi ...................... 378/62 |
| 2012/0288056 | A1 * | 11/2012 | Murakoshi et al. ............. 378/37 |
| 2013/0032727 | A1 * | 2/2013  | Kondoh ......................... 250/394 |

FOREIGN PATENT DOCUMENTS

| JP | 2005156511 A | 6/2005 |
| JP | 2009543080 A | 12/2009 |
| JP | 2010063646 A | 3/2010 |
| JP | 2011224329 A | 11/2011 |
| WO | 2008006470 A1 | 1/2008 |

* cited by examiner

*Primary Examiner* — Robert Kim
*Assistant Examiner* — Eliza Osenbaugh-Stewar
(74) *Attorney, Agent, or Firm* — Canon USA Inc. IP Division

(57) ABSTRACT

An X-ray imaging apparatus includes a diffraction grating that forms an interference pattern by diffracting X-rays emitted from an X-ray source, an absorption grating that shields a portion of the interference pattern, a detector that detects the X-rays emitted from the absorption grating, and a moving unit that changes relative positions of a sample object and the absorption grating. The moving unit changes the relative positions of the sample object and the absorption grating from first relative positions to second relative positions. The detector detects the X-rays at least when the sample object and the absorption grating are at the first relative positions and when the sample object and the absorption grating are at the second relative positions.

15 Claims, 3 Drawing Sheets

X-RAY IMAGING APPARATUS

BACKGROUND OF THE INVENTION

1. Field of the Invention

The present invention relates to an X-ray imaging apparatus.

2. Description of the Related Art

X-ray phase imaging is a method of acquiring information on a sample object by producing contrast on the basis of shifting the phase of X-rays. One of such X-ray phase imaging methods is Talbot interferometry.

Talbot interferometry requires at least the following components: an X-ray source that emits spatially coherent X-rays, a diffraction grating that periodically modulates the phase of the X-rays, and a detector. When spatially coherent X-rays are transmitted through the diffraction grating, the phase of the X-rays periodically changes in correspondence with the shape of the diffraction grating. This change forms an interference pattern called a self image at a certain distance called Talbot distance from the diffraction grating. A sample object is positioned between the X-ray source and the diffraction grating or between the diffraction grating and the detector. Since the shape and the refractive index of the sample object influence the self image, the self image is deformed. Information on the phase of X-rays transmitted through the sample object (hereinafter also referred to as phase information) can be acquired on the basis of the deformation of the self image. Exemplary phase information on the sample object include a differential phase image, a phase image, and a scattering image.

In general, the pitch of a self image formed in Talbot interferometry using X-rays is generally smaller than the pixel pitch of the detector. Therefore, it is difficult to directly detect the self image. Hence, an absorption grating is used. The absorption grating has a periodic structure in which shielding portions that block X-rays and transmissive portions that transmit X-rays are periodically arranged. That is, a moire pattern is formed by shielding some portions of the self image with the absorption grating; the resultant moire pattern is detected for phase retrieval. In this manner, phase information on the sample object is acquired.

To form a moire pattern by using the self image and the absorption grating, the shielding portions of the absorption grating need to block X-rays to such an extent that a moire pattern is formed, and the period of the shielding portions and the transmissive portions needs to be substantially the same as the period of the self image.

PCT Japanese Translation Patent Publication No. 2009-543080 (International Publication No. WO2008006470, counterpart to publication: US2009/0316857) discloses an X-ray imaging apparatus including an absorption grating in which structures made of a material, such as resist or silicon (Si), having a high transmittance to X-rays are provided and gaps between the structures are filled with gold plate.

Gold plating, which is employed in the structure disclosed by PCT Japanese Translation Patent Publication No. 2009-543080 (International Publication No. WO2008006470, counterpart to publication: US2009/0316857), is suitable for fabrication of an absorption grating including shielding portions that are made of gold and each have a high aspect ratio.

Nevertheless, in the fabrication of such a gold-plated absorption grating, chipping of the mold and deposition of plating metal on the surface of the mold may occur, leading to irregularities in the period of the periodic structure. If the periodic structure includes any regions having irregularities in the period thereof, a desired moire pattern cannot be formed. That is, an imaging area may include portions from which phase information on the sample object is difficult to acquire through the detection of deformation in the self image of the sample object.

SUMMARY OF THE INVENTION

The present invention provides an X-ray imaging apparatus capable of easily acquiring phase information on any regions of a sample object that is difficult to acquire because of the use of an absorption grating including any regions having irregularities in the period of a periodic structure thereof.

An imaging apparatus according to an aspect of the present invention includes a diffraction grating that forms an interference pattern by diffracting X-rays emitted from an X-ray source, an absorption grating that shields a portion of the interference pattern, a detector that detects the X-rays emitted from the absorption grating, and a moving unit that changes relative positions of a sample object and the absorption grating. The sample object is positioned between the X-ray source and the diffraction grating or between the diffraction grating and the absorption grating. The moving unit changes the relative positions of the sample object and the absorption grating from first relative positions to second relative positions. The detector detects the X-rays at least when the sample object and the absorption grating are at the first relative positions and when the sample object and the absorption grating are at the second relative positions. The second relative positions correspond to relative positions of the sample object and the absorption grating in at least one of a state where the sample object and the absorption grating have been moved relative to each other from the first relative positions in a periodic direction of the absorption grating by a length corresponding to an integral multiple of a period of the absorption grating and a state where the sample object and the absorption grating have been rotated relative to each other from the first relative positions in a plane perpendicular to an X-ray axis by an angle corresponding to an integral multiple of 180/n degrees. The n denotes the number of periodic directions of the absorption grating.

Further features of the present invention will become apparent from the following description of exemplary embodiments with reference to the attached drawings.

DESCRIPTION OF THE EMBODIMENTS

General Embodiment

A general embodiment of the present invention concerns an X-ray imaging apparatus that includes an absorption grating including any regions having irregularities in the period of a periodic structure thereof and that is configured to change the relative positions of the absorption grating and a sample object, by moving the absorption grating. Changing the relative positions of the absorption grating and the sample object changes regions of the sample object influenced by the regions of the periodic structure having irregularities in the period. Hence, the influence of the regions of the periodic structure having irregularities in the period becomes dispersed. Consequently, phase information on the regions of the sample object that are influenced by the regions of the periodic structure having irregularities in the period is acquired more easily than in the related-art techniques.

Figure 1:
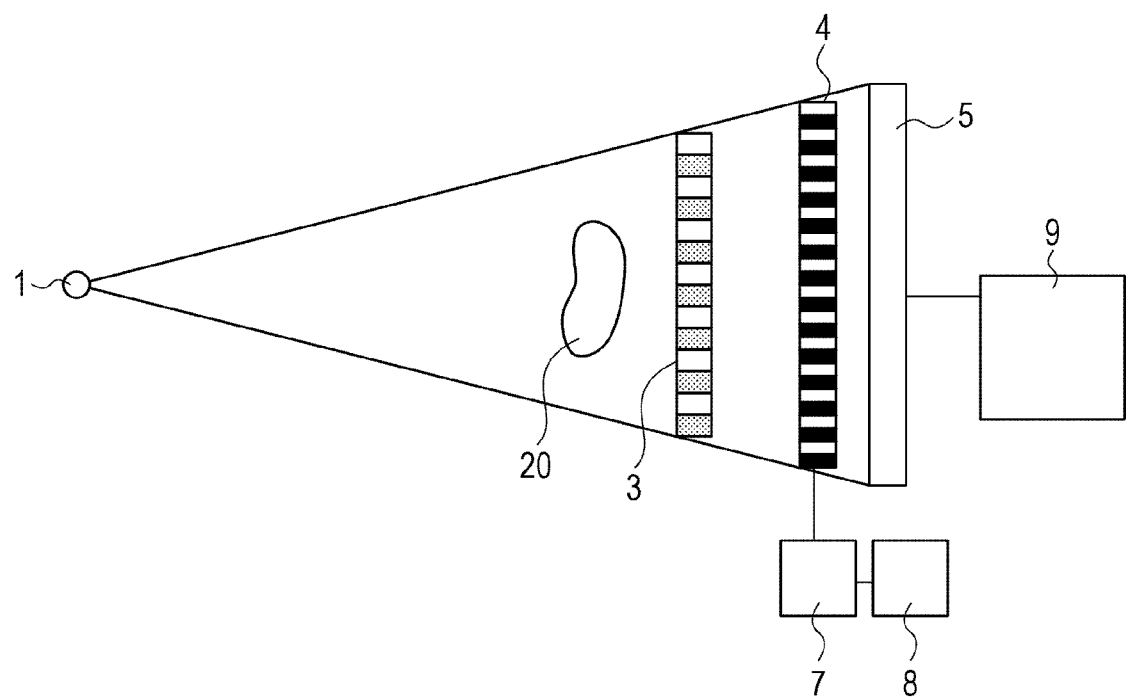
FIG. 1 is a schematic diagram of an X-ray imaging apparatus according to an exemplary embodiment of the present invention.

FIG. 1 illustrates an exemplary configuration of the X-ray imaging apparatus according to an exemplary embodiment. The X-ray imaging apparatus illustrated in FIG. 1 includes an X-ray source 1, a diffraction grating 3 that diffracts X-rays and thus forms a self image, an absorption grating 4 that shields portions of the self image, a detector 5 that detects X-rays, and a moving unit that moves the absorption grating 4. The moving unit of the X-ray imaging apparatus according to the general embodiment includes an actuator 7 connected to the absorption grating 4, and an adjusting unit 8 that adjusts the movement of the absorption grating 4 realized by the actuator 7. The detector 5 is connected to an arithmetic unit 9 that performs calculations on the basis of the results of detection and thus acquires phase information on the sample object. Such acquisition of phase information on the sample object from the results of detection is referred to as phase retrieval.

The elements included in the X-ray imaging apparatus will now be described individually.

X-rays emitted from the X-ray source 1 according to the general embodiment may be continuous X-rays or characteristic X-rays. X-rays referred to herein are electromagnetic waves at 2 keV or higher and 100 keV or lower.

A wavelength selective filter or a source grating that splits X-rays may be provided additionally on the path of the X-rays emitted from the X-ray source 1.

The X-rays emitted from the X-ray source 1 need to be formed into a self image after being diffracted by the diffraction grating 3 and therefore need to be spatially coherent enough to form a self image.

When the X-rays emitted from the X-ray source 1 are transmitted through a sample object 20, the phase of the X-rays changes in accordance with the refractive index and the shape of the sample object 20. The sample object 20 may be provided at any position between the X-ray source 1 and the absorption grating 4. In FIG. 1, the sample object 20 is positioned between the X-ray source 1 and the diffraction grating 3. Alternatively, the sample object 20 may be positioned between the diffraction grating 3 and the absorption grating 4.

When the X-rays are diffracted by the diffraction grating 3, an interference pattern called a self image is formed at a certain distance called Talbot distance from the diffraction grating 3. This self image is a pattern in which bright areas and dark areas are periodically formed in correspondence with periodic changes in the intensity of X-rays. In this specification, areas of the self image where the intensity of X-rays is high are referred to as bright areas, and areas of the self image where the intensity of X-rays is low are referred to as dark areas. The diffraction grating 3 used in the general embodiment is a phase diffraction grating and has a periodic structure in which advance phase portions and lag phase portions are periodically arranged. The diffraction grating 3 may alternatively be an amplitude diffraction grating that modulates the intensity of X-rays, although the amount of loss of X-rays is smaller in the phase diffraction grating. The lag phase portions and the advance phase portions of the diffraction grating 3 may be arranged either one-dimensionally or two-dimensionally.

The phase of X-rays transmitted through the lag phase portions is shifted by $\pi$ or $\pi/2$ radians with respect to the phase of X-rays transmitted through the advance phase portions. The amount of phase shift may be any other value.

The absorption grating 4 has a periodic structure in which shielding portions 10 that block X-rays and transmissive portions 11 that transmit X-rays are periodically arranged. In this manner, the absorption grating 4 shields some of the bright areas of the self image formed by the diffraction grating 3. Note that a situation (state) where the shielding portions 10 and the transmissive portions 11 are periodically arranged refers to either, in a region of the absorption grating 4 where the periodic structure is provided, a situation where the shielding portions 10 and the transmissive portions 11 are arranged at the same pitch or a situation where the shielding portions 10 and the transmissive portions 11 are arranged at a variable pitch that changes with a certain regularity. For example, a situation where the pitch of the shielding portions 10 and the transmissive portions 11 is continuously reduced toward the center also corresponds to a situation where the shielding portions 10 and the transmissive portions 11 are periodically arranged.

Figure 2A:
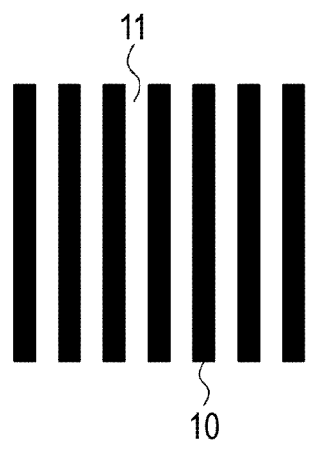
FIGS. 2A to 2D are schematic diagrams of exemplary absorption gratings according to an exemplary embodiment of the present invention.

The period of the shielding portions 10 and the transmissive portions 11, and a direction in which these portions are arranged are determined by the shape of the self image and the shape of a desired moire pattern. In this specification, a moire pattern encompasses a moire pattern whose period has an infinite length or a substantially infinite length. That is, the present invention is also applicable to a case where the period of a moire pattern is not observed clearly from a single image showing the result of detection. FIGS. 2A and 2B illustrate examples of the absorption grating 4. The absorption grating 4 illustrated in FIG. 2A has a one-dimensional periodic structure in which the shielding portions 10 and the transmissive portions 11 are arranged periodically in one direction. As with the diffraction grating 3, the absorption grating 4 may alternatively have a two-dimensional periodic structure in which the shielding portions 10 and the transmissive portions 11 are arranged periodically in two directions. For example, the absorption grating 4 may have a periodic pattern defined by crisscrossing parallel lines (not shown), or a checkered pattern of shielding portions 10 and transmissive portions 11 (as illustrated in FIG. 2B).

The shielding portions 10 of the absorption grating 4 are made of a material having a low transmittance to X-rays, such as gold, platinum, tungsten, tantalum, molybdenum, or the like, or an alloy containing any of the foregoing. The transmissive portions 11 are made of a material having a high transmittance to X-rays, for example, resin such as photosensitive resist, or silicon (Si). The transmissive portions 11 may alternatively be hollow cavities devoid of any material.

The shielding portions 10 do not need to block X-rays completely but need to block X-rays to such an extent as to form a moire pattern by shielding some portions of the self image. Hence, even in the above case where the shielding portions 10 of the absorption grating 4 are made of a material having a low transmittance to X-rays, the shielding portions 10 each need to have a high aspect ratio (the length in the direction of the X-ray axis/the width in the direction of periodic arrangement).

The absorption grating 4 can be fabricated by plating. Structures made of photosensitive resist or Si and each having a high aspect ratio are formed on a flat surface of a substrate. Subsequently, gaps between the structures are filled with plating metal.

Alternatively, the structures each having a high aspect ratio may be formed by etching a silicon substrate, and gaps between the structures may be filled with plating metal. The high-aspect-ratio structures thus formed correspond to the transmissive portions 11.

The plating metal may be any material having a low transmittance to X-rays. Gold or platinum is relatively easy to plate. Structures made of the plating metal provided in the gaps between the high-aspect-ratio structures correspond to the shielding portions 10.

In fabricating the absorption grating 4, the arrangement of the shielding portions 10 and the transmissive portions 11 may have irregularities partially. Irregularities in the arrangement of the shielding portions 10 and the transmissive portions 11 referred to herein occur in the following two situations, roughly: a situation where any shielding portions 10 are present at any of the positions where X-rays are to be transmitted, that is, the positions where the transmissive portions 11 are to be present; and a situation where any transmissive portions 11 are present at any of the positions where X-rays are to be blocked, that is, the positions where the shielding portions 10 are to be present.

If any X-ray shielding member is present on a line connecting the X-ray source 1 and a position where a transmissive portion 11 is to be present, a shielding portion 10 is formed at the position where a transmissive portion 11 is to be present. If a shielding portion 10 is present at the position where a transmissive portion 11 is to be present, X-rays to be allowed to pass therethrough are blocked. Thus, shielding portions 10 may be formed at unintended positions because of the following reason. During the fabrication of the absorption grating 4, some of the structures corresponding to the transmissive portions 11 are chipped off, where plating metal deposits. In another case, plating metal deposits in a mushroom-like shape on some of the structures corresponding to the transmissive portions 11.

If no X-ray shield member is present on a line connecting the X-ray source 1 and a position where a shielding portion 10 is to be present, a transmissive portion 11 is formed at the position where a shielding portion 10 is to be present. If a transmissive portion 11 is present at the position where a shielding portion 10 is to be present, X-rays to be blocked are allowed to pass therethrough. Thus, transmissive portions 11 may be formed at unintended positions because of the presence of resist residues, plating failure due to adhesion of dust on the surfaces of some of the structures corresponding to the transmissive portions 11 prior to plating, or the like.

Figure 2C:
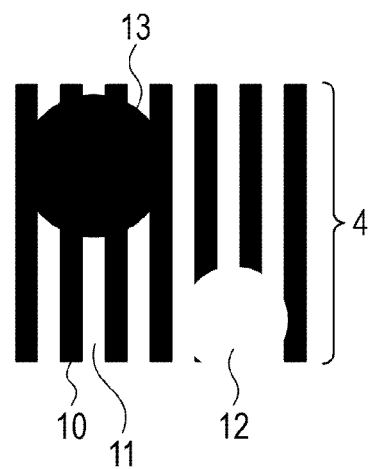
Figure 2B:
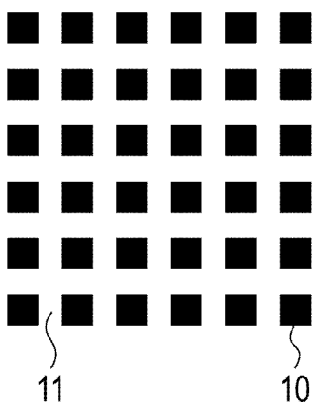

The absorption grating 4 illustrated in FIG. 2C has a circular shielding portion 13 formed as a result of deposition of plating metal. As illustrated in FIG. 2C, the circular shielding portion 13 has a diameter larger than the period of the periodic structure. That is, the circular shielding portion 13 extends over some positions where transmissive portions 11 are to be present. If the circular shielding portion 13 is of a size larger than the pixel size of the detector 5 and X-rays to be detected by a corresponding one of the pixels are all blocked, information on changes in the intensity of X-rays for that pixel cannot be acquired. Consequently, information on the deformation of the moire pattern caused by the sample object has a missing part. In contrast, if a transmissive portion, such as a circular transmissive portion 12 illustrated in FIG. 2C, extends over positions where shielding portions 10 are to be present, X-rays to be blocked are allowed to pass therethrough and the X-rays thus transmitted through those positions enter the detector 5 while retaining a corresponding portion of the self image, not forming a moire pattern. In general, changes in the period of a self image tend to be smaller than the pixel size. Hence, information on changes in the self image of a sample object tends to have a missing part.

A region, such as the circular shielding portion 13 or the circular transmissive portion 12, of the absorption grating 4 where the arrangement of the shielding portions 10 and the transmissive portions 11 has any irregularities is herein referred to as irregularly arranged region. The irregularly arranged region may have any shape.

Figure 2D:
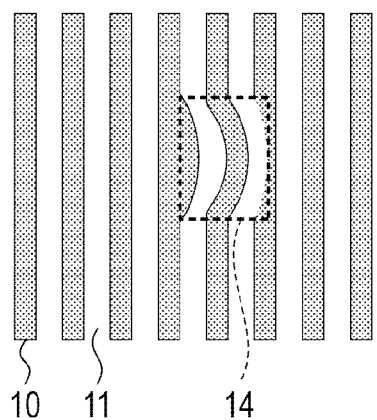

Even in a region that is free of any transmissive portions and shielding portions such as those illustrated in FIG. 2C each having a size larger than the period of the periodic structure, a shielding portion may be present at a position where a transmissive portion 11 is to be present, or a transmissive portion may be present at a position where a shielding portion 10 is to be present. For example, FIG. 2D illustrates a region 14 in which the periodic structure is distorted. The region 14 is also referred to as irregularly arranged region.

Even if the irregularly arranged region is of a size smaller than the pixel size, the amount of information acquired from a pixel corresponding to that region is reduced because of the presence of that region. This may influence the phase information on the sample object 20 to be acquired.

In the general embodiment, the absorption grating 4 including any irregularly arranged regions as illustrated in FIG. 2C is used. Furthermore, the absorption grating 4 is moved by the actuator 7 so that the relative positions of the sample object 20 and the absorption grating 4 are changed, whereby the influence of the irregularly arranged regions on the phase information of the sample object 20 is made dispersed. The length and direction of the movement of the absorption grating 4 realized by the actuator 7 are adjusted in accordance with signals from the adjusting unit 8.

When the absorption grating 4 is moved by the actuator 7, the relative positions of the sample object 20 and the absorption grating 4 are changed at least from first relative positions to second relative positions.

Assuming that the absorption grating 4 has a one-dimensional periodic structure as illustrated in FIG. 2C, one can define a periodic direction by taking into account the direction in which the periodic structures are arranged. Therefore, in FIG. 2C, if the periodic direction is defined as the x direction, an in-plane direction of the absorption grating 4 that is perpendicular to the periodic direction is the y direction. That is, in general, the periodic direction (direction in which the periodic structures are arranged) is perpendicular to the in-plane direction. When the relative positions of the absorption grating 4 and the sample object 20 are changed from the first relative positions to the second relative positions, the absorption grating 4 may be moved either translationally in the x direction or along an x-y plane. The x-y plane is perpendicular to the axis of X-rays connecting the center of the X-ray source 1 and the center of the detector 5. If the absorption grating 4 is moved along the x-y plane, the imaging area can be enlarged also in the y direction. In general, however, the larger the length of movement, the more difficult to maintain accuracy. Therefore, the direction and the length of movement of the absorption grating 4 are appropriately determined in accordance with the size of the periodic structure provided in the absorption grating 4 to be used and the specifications of the moving unit to be used.

The influence of any irregularly arranged regions can be made dispersed if a portion of the periodic structure that is free of any irregularly arranged regions when the absorption grating 4 and the sample object 20 are at the second relative positions is present at each of any positions where the periodic structure has irregularly arranged regions when the absorption grating 4 and the sample object 20 are at the first relative positions. Such a situation occurs when the distance of relative movement between the sample object 20 and the absorption grating 4 in the periodic direction of the absorption grating 4 is larger than the length of an irregularly arranged region of the absorption grating 4 in the periodic direction of the absorption grating 4 and is smaller than the length of a regularly arranged region of the absorption grating 4 in the periodic direction of the absorption grating 4. If there are a plurality of irregularly arranged regions, the distance of relative movement between the sample object 20 and the absorption grating 4 can be made larger than the length of the largest one of the plurality of irregularly arranged regions.

Even if the distance of relative movement between the sample object 20 and the absorption grating 4 is smaller than the length of such an irregularly arranged region, the advantageous effects of the present invention are produced. Specifically, even if the distance of relative movement between the sample object 20 and the absorption grating 4 is smaller than the length of the irregularly arranged region, the influence of the irregularly arranged region can be mostly made dispersed as long as the difference between the two is smaller than the pixel size of the detector 5. Hence, the phase information on the sample object 20 to be acquired is less influenced. After a plurality of absorption gratings 4 are fabricated, any irregularly arranged regions of the periodic structure can be measured for each of the absorption gratings 4. Therefore, the length of movement can be set for each of the absorption gratings 4.

When the absorption grating 4 is moved from the first relative position to the second relative position, the absorption grating 4 may be rotated in the x-y plane, instead of being moved translationally in the x direction. In the case where the absorption grating 4 is rotated, a portion of the periodic structure that is free of any irregularly arranged regions when the absorption grating 4 and the sample object 20 are at the second relative positions can be present at each of any positions where the periodic structure has irregularly arranged regions when the absorption grating 4 and the sample object 20 are at the first relative positions. Such a situation occurs when, for example, the absorption grating 4 is rotated relative to the sample object 20 about a position that is free of irregularly arranged regions.

Alternatively, the relative positions of the sample object 20 and the absorption grating 4 may be changed both with a translational movement of the absorption grating 4 in the x direction or a movement of the absorption grating 4 in the x-y plane and with a rotational movement of the absorption grating 4 in the x-y plane. Moreover, the actuator 7 may move not only the absorption grating 4 but also the diffraction grating 3 and/or the detector 5.

When the relative positions of the sample object 20 and the absorption grating 4 are changed from the first relative positions to the second relative positions, the relative positions of the sample object 20 and the irregularly arranged region of the absorption grating 4 also change. Therefore, the influence of the irregularly arranged region is made dispersed within the imaging area. Even if the relative positions of the sample object 20 and the absorption grating 4 are changed from the first relative positions to the second relative positions, the moire pattern formed by the self image and the absorption grating 4 needs to be unchanged, although changes due to the movement of any irregularly arranged regions are allowed. The change from the first relative positions to the second relative positions will now be described more specifically.

First, a case will be described in which the relative positions of the absorption grating 4 and the sample object 20 are changed with a translational movement in the x direction or a movement in the x-y plane.

To keep the moire pattern formed by the self image and the absorption grating 4 unchanged while allowing changes due to the movement of any irregularly arranged regions, the relative positions of the absorption grating 4 and the sample object 20 are changed in the x direction by a length corresponding to an integral multiple of the period of the absorption grating 4. That is, the second relative positions of the absorption grating 4 and the sample object 20 correspond to positions of the absorption grating 4 and the sample object 20 that have been moved relative to each other from the respective first relative positions in the x-direction by a length corresponding to an integral multiple of the period of the absorption grating 4.

A case where the absorption grating 4 is moved while the sample object 20 is fixed will now be described. In this case, the length of movement of the absorption grating 4 at the change in the relative positions of the absorption grating 4 and the sample object 20 from the first relative positions to the second relative positions corresponds to an integral multiple of the period of the absorption grating 4. In a case where the absorption grating 4 has a two-dimensional periodic structure, the absorption grating 4 can be said to have two periodic directions. That is, the periodic structures in the absorption grating 4 are arranged in two directions. However, in this case, the absorption grating 4 is moved translationally in only one of the two periodic directions (in the x direction) so that each of any irregularly arranged regions is moved. In a case where the absorption grating 4 is moved translationally in both of the two periodic directions (in the x-y plane), the relative positions of the sample object 20 and the absorption grating 4 need to change by a length corresponding to an integral multiple of the period of the absorption grating 4 in both of the two periodic directions of the absorption grating 4 along with the change in the relative position of the absorption grating 4 from the first relative position to the second relative position.

In the general embodiment, the absorption grating 4 is moved in the periodic direction thereof by a length corresponding to an integral multiple of the period thereof while the sample object 20 is fixed. Alternatively, the sample object 20 or both the absorption grating 4 and the sample object 20 may be moved, as long as the difference in the length of movement in the periodic direction of the absorption grating 4 between the sample object 20 and the absorption grating 4 becomes a length corresponding to an integral multiple of the period of the absorption grating 4.

With such changes in the relative positions of the sample object 20 and the absorption grating 4, the region of the sample object 20 that is influenced by each irregularly arranged region of the absorption grating 4 also changes. Accordingly, the influence is made dispersed. Furthermore, the relative positions of the sample object 20 and the absorption grating 4 are changed by a length corresponding to an integral multiple of the period of the absorption grating 4 in the periodic direction of the absorption grating 4. This prevents X-rays having information on some regions of the sample object 20 from forming any bright areas or dark areas in the self image because of the change in the relative positions of the sample object 20 and the absorption grating 4.

To keep the moire pattern unchanged even if the relative positions of the sample object 20 and the absorption grating 4 are changed from the first relative positions to the second relative positions, the relative positions of the self image and the absorption grating 4 are kept unchanged in the periodic direction of the absorption grating 4. To keep the relative positions of the self image and the absorption grating 4 unchanged, the diffraction grating 3 can be moved such that the length of movement of the self image corresponds to the length of movement of the absorption grating 4. If divergent X-rays are used, the distance from the X-ray source 1 to the absorption grating 4 is larger than the distance from the X-ray source 1 to the diffraction grating 3. In such a case, it should be taken into consideration that the self image formed on the absorption grating 4 is enlarged.

Even if the relative positions of the self image and the absorption grating 4 are changed by a length corresponding to an integral multiple of the period of the absorption grating 4 in the periodic direction of the absorption grating 4, the moire pattern formed by the self image and the absorption grating 4 does not change, although changes due to the movement of any irregularly arranged regions are allowed. To change the relative positions of the self image and the absorption grating 4 by a length corresponding to an integral multiple of the period of the absorption grating 4, only the absorption grating 4 may be moved in the periodic direction thereof by a length corresponding to an integral multiple of the period thereof while the self image is fixed. Alternatively, both the self image and the absorption grating 4 may be moved such that the difference in the length of movement between the two becomes a length corresponding to an integral multiple of the period of the absorption grating 4 in the periodic direction of the absorption grating 4.

Another case will now be described where the absorption grating 4 is rotated only in the x-y plane without any translational movement in the x direction or any other movement in the x-y plane. To keep the moire pattern formed by the self image and the absorption grating 4 unchanged while allowing changes due to the movement of any irregularly arranged regions, the sample object 20 and the absorption grating 4 are rotated relative to each other in the x-y plane by an angle corresponding to an integral multiple of 180/n degrees. That is, the second relative positions of the sample object 20 and the absorption grating 4 correspond to positions of the sample object 20 and the absorption grating 4 that have been rotated relative to each other from the respective first relative positions in the x-y plane by an angle corresponding to an integral multiple of 180/n degrees, where n denotes the number of periodic directions of the absorption grating 4. That is, if the absorption grating 4 has a one-dimensional periodic structure, n is 1. If the absorption grating 4 has a two-dimensional periodic structure, n is 2.

In the case illustrated in FIG. 2A where the periodic structure of the absorption grating 4 includes the shielding portions 10 and the transmissive portions 11 that are one-dimensionally arranged, when the relative positions of the sample object 20 and the absorption grating 4 are changed from the first relative positions to the second relative positions, the absorption grating 4 is not rotated or is rotated by 180 degrees relative to the sample object 20.

In the case illustrated in FIG. 2B where the absorption grating 4 has a two-dimensional periodic structure, when the relative positions of the sample object 20 and the absorption grating 4 are changed from the first relative positions to the second relative positions, the absorption grating 4 is rotated by an angle corresponding to an integral multiple of 90 degrees relative to the sample object 20, i.e., by 90 degrees, 180 degrees, or 270 degrees, or is not rotated relative to the sample object 20. The sample object 20 and the absorption grating 4 may be moved relative to each other translationally in the x direction or in any other direction in the x-y plane while being rotated in the x-y plane. In that case, to keep the moire pattern formed by the self image and the absorption grating 4 unchanged while allowing changes due to the movement of any irregularly arranged regions, the relative positions of the absorption grating 4 and the sample object 20 are changed in the x direction by a length corresponding to an integral multiple of the period of the absorption grating 4 while the sample object 20 and the absorption grating 4 are rotated relative to each other by an angle corresponding to an integral multiple of 180/n degrees.

In the X-ray imaging apparatus according to the general embodiment, the detector 5 detects X-rays in conjunction with the movement of the absorption grating 4 described above.

The detector 5 detects information on the intensity of X-rays and detects the distribution of intensity of a moire pattern formed by the self image and the absorption grating 4. The detection is performed in conjunction with the movement of the absorption grating 4 realized by the actuator 7 and at least when the sample object 20 and the absorption grating 4 are at the first relative positions and at the second relative positions. The detection may be performed for each of the first relative positions and the second relative positions. Alternatively, the relative positions of the sample object 20 and the absorption grating 4 may be changed from the first relative positions to the second relative positions in a single detecting action.

If the detection is performed for each of the first relative positions and the second relative positions, the result of detection of a moire pattern formed at the first relative positions and the result of detection of a moire pattern formed at the second relative positions are obtained independently of each other.

If the relative positions of the sample object 20 and the absorption grating 4 are changed in a single detecting action, the result of detection of a moire pattern formed at the first relative positions and the result of detection of a moire pattern formed at the second relative positions are combined into a single result of detection. In general, a detector generates noise in every detecting action (every time a result of detection is obtained). Therefore, if the relative positions of the sample object 20 and the absorption grating 4 are changed in a single detecting action, the generation of noise can be suppressed more than in the case where detection is performed for each of the different relative positions. In the case where the relative positions of the sample object 20 and the absorption grating 4 are changed in a single detecting action, if the sample object 20 is prevented from being irradiated with X-rays while the sample object 20 and the absorption grating 4 are being moved relative to each other, the occurrence of blurring in the result of detection due to the movement of the absorption grating 4 is prevented. To prevent the sample object 20 from being irradiated with X-rays, the emission of X-rays from the X-ray source 1 may be stopped or a shutter may be provided between the X-ray source 1 and the sample object 20 so as to shield the sample object 20 from X-rays. The shutter is made of a material having a high X-ray absorption, such as lead, with a thickness sufficient for blocking X-rays to be used. The shutter may alternatively be provided between the sample object 20 and the detector 5, not between the X-ray source 1 and the sample object 20. In such a case also, the occurrence of blurring in the result of detection due to the movement of the absorption grating 4 is prevented. If the exposure of the sample object 20 to X-rays needs to be reduced, it is appropriate to prevent the sample object 20 from being irradiated with X-rays as described above.

If the time required for moving the absorption grating 4 is short enough relative to imaging time, the influence of the blurring caused by the movement of the absorption grating 4 is small. In such a case, the sample object 20 may be kept irradiated with X-rays while the absorption grating 4 is being moved.

In the general embodiment, the moire pattern does not change with the change in the relative positions of the sample object 20 and the absorption grating 4 from the first relative positions to the second relative positions.

Therefore, phase retrieval is performable on the basis of the combination of the result of detection obtained at the first relative positions and the result of detection obtained at the second relative positions whether the detection is performed for every change in the relative positions or the relative positions are changed in a single detecting action. Hence, phase retrieval can be done at a time. Moreover, the combination of the results of detection only needs to have a level of contrast that enables phase retrieval. Therefore, the probability that the amount of X-ray application to the sample object 20 can be reduced is higher than in a case where the moire pattern changes with the changes from the first relative positions to the second relative positions. In the case where the moire pattern changes with the changes in the relative positions, phase retrieval is necessary for each of the results of detection and the results of the individual phase retrievals need to be integrated at the end of the process. That is, phase retrieval needs to be performed for a plurality of number of times, and a level of contrast that enables phase retrieval needs to be realized for every detecting action.

The arithmetic unit 9 is connected to the detector 5 and performs calculations for phase retrieval by using the result of detection obtained from the detector 5, thereby acquiring phase information on the sample object 20. In the general embodiment, phase retrieval is performed through Fourier transformation. Specifically, information on a differential phase image of the sample object 20 is acquired from the result of detection and the information is integrated, whereby a phase image is acquired. Alternatively, for example, only the differential phase image may be acquired.

In a case where Fourier transformation is employed, the result of detection is Fourier-transformed and a spatial frequency spectrum is acquired. Subsequently, a component derived from a carrier frequency is extracted from the spatial frequency spectrum, and the component is inversely Fourier-transformed. Thus, differential phase information on the sample object 20 is acquired. In the general embodiment, the differential phase image and the phase image of the sample object 20 are acquired through Fourier transformation. Another method, for example, fringe scanning, may alternatively be employed.

An X-ray imaging method employed in the X-ray imaging apparatus according to the general embodiment will now be described with reference to FIG. 3. The following process is realized in accordance with a program performed by a central processing unit (CPU) included in the arithmetic unit 9, unless otherwise stated.

Figure 3:
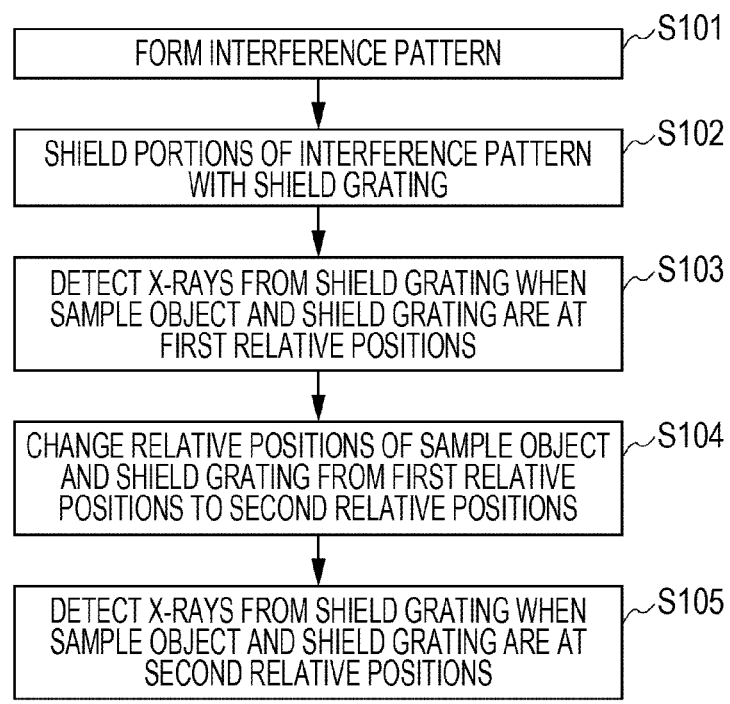
FIG. 3 is a flowchart of an X-ray imaging method employed in the X-ray imaging apparatus according to an exemplary embodiment of the present invention.

FIG. 3 is a flowchart of the X-ray imaging method employed in the X-ray imaging apparatus according to the general embodiment.

The X-ray imaging method includes a step of forming an interference pattern by diffracting X-rays emitted from the X-ray source 1 (step S101), a step of shielding portions of the interference pattern with the absorption grating 4 (step S102), a step of detecting X-rays emitted from the absorption grating 4 when the sample object 20 and the absorption grating 4 are at the first relative positions (step S103), a step of changing the relative positions of the sample object 20 and the absorption grating 4 from the first relative positions to the second relative positions (step S104), and a step of detecting X-rays emitted from the absorption grating 4 when the sample object 20 and the absorption grating 4 are at the second relative positions (step S105).

The step of detecting X-rays emitted from the absorption grating 4 when the sample object 20 and the absorption grating 4 are at the first relative positions (step S103) and the step of detecting X-rays emitted from the absorption grating 4 when the sample object 20 and the absorption grating 4 are at the second relative positions (step S105) may be performed in a single detecting action of the detector 5. That is, the step of changing the relative positions of the sample object 20 and the absorption grating 4 from the first relative positions to the second relative positions (step S104) may be performed during exposure performed by the detector 5. If the step of changing the relative positions of the sample object 20 and the absorption grating 4 from the first relative positions to the second relative positions (step S104) is performed during exposure, the result of detection of a moire pattern formed when the sample object 20 and the absorption grating 4 are at the first relative positions and the result of detection of a moire pattern formed when the sample object 20 and the absorption grating 4 are at the second relative positions are combined.

The step of detecting X-rays emitted from the absorption grating 4 when the sample object 20 and the absorption grating 4 are at the first relative positions (step S103) and the step of detecting X-rays emitted from the absorption grating 4 when the sample object 20 and the absorption grating 4 are at the second relative positions (step S105) may be performed separately. That is, after starting and ending the exposure performed by the detector 5 when the sample object 20 and the absorption grating 4 are at the first relative positions, the step of changing the relative positions (step S104) may be performed, followed by the step of detecting X-rays emitted from the absorption grating 4 when the sample object 20 and the absorption grating 4 are at the second relative positions (step S105). If imaging is performed in such an imaging process, the result of detection of a moire pattern formed when the sample object 20 and the absorption grating 4 are at the first relative positions and the result of detection of a moire pattern formed when the sample object 20 and the absorption grating 4 are at the second relative positions are acquired independently of each other.

First Exemplary Embodiment

A first exemplary embodiment of the present invention concerns an exemplary method of acquiring phase information on the sample object 20 by using a diffraction grating and an absorption grating each having a one-dimensional period.

The configuration of the X-ray imaging apparatus is as illustrated in FIG. 1, the same as that according to the general embodiment. The diffraction grating 3 has a periodic structure in which advance phase portions and lag phase portions are arranged with a one-dimensional period at a pitch of 7.35 µm. In this periodic structure, the advance phase portions and the lag phase portions have the same width. The phase of X-rays transmitted through the advance phase portions is in advance of the phase of X-rays transmitted through the lag phase portions by $\pi$ radians. Such a diffraction grating 3 can be fabricated by etching a Si wafer.

The absorption grating 4 has a periodic structure that is a square of side 50 mm and in which the shielding portions 10 and the transmissive portions 11 are arranged at a pitch of 4.0 µm. The absorption grating 4 can be fabricated as follows. For example, a substrate made of resin such as silicon is patterned through exposure with X-rays, and the resultant resin mold is gold-plated. Some of the shield structures made of gold plate have on the surfaces thereof hemispherical gold deposits having a diameter of 40 μm at maximum. Regions having such gold deposits each correspond to the irregularly arranged region in the first exemplary embodiment.

Suppose that the distance from the X-ray source 1 to the diffraction grating 3 is 1170 mm, the distance from the diffraction grating 3 to the absorption grating 4 is 104 mm, the detector 5 is positioned immediately after the absorption grating 4, and the pixel pitch of the detector 5 is 50 μm. The area to be irradiated with X-rays is defined, by providing a light shielding member made of lead, so as to be an area in which the periodic structures of the diffraction grating 3 and the absorption grating 4 are provided.

When X-rays are applied to the diffraction grating 3, a self image formed by the diffraction grating 3 is transmitted through the absorption grating 4 and is detected as a moire pattern by the detector 5. The pitch and the periodic direction of the moire pattern are adjustable by adjusting the relative positions of the diffraction grating 3 and the absorption grating 4 and the angles of the periodic directions of the diffraction grating 3 and the absorption grating 4 with respect to the detector 5. In the first exemplary embodiment, the positions of the diffraction grating 3, the absorption grating 4, and the detector 5 are adjusted such that the pitch of the moire pattern is 200 μm, which corresponds to four pixels of the detector 5.

In the related art, phase information is acquired through Fourier transformation by using the result of a single detecting action realized without moving any of the X-ray source, the sample object, the diffraction grating, the absorption grating, and the detector. In such a case, the phase information may have a missing part around pixels corresponding to any irregularly arranged regions of the absorption grating. In the first exemplary embodiment, imaging is performed while the absorption grating 4 is moved in the periodic direction of the absorption grating 4 twice by 44 μm, which is eleven times the pitch of the absorption grating 4, at a time. An imaging method employed in the X-ray imaging apparatus according to the first exemplary embodiment will now be described briefly.

First, the sample object 20 and the absorption grating 4 are set at the first relative positions, and X-rays are applied from the X-ray source 1 to the sample object 20. Then, a moire pattern whose phase has been modulated while being influenced by the sample object 20 is detected by the detector 5.

While the state of detection of the detector 5 is retained, the application of X-rays to the sample object 20 is stopped and the absorption grating 4 is moved in the periodic direction thereof by 44 μm, whereby the sample object 20 and the absorption grating 4 are set at the second relative positions. After moving the absorption grating 4, X-rays are applied to the sample object 20 again. Since the state of detection of the detector 5 is retained, X-rays enter the detector 5 again. Hence, a moire pattern formed when the sample object 20 and the absorption grating 4 are at the second relative positions is detected.

While the state of detection of the detector 5 is still retained, the application of X-rays is stopped and the absorption grating 4 is moved in the periodic direction thereof by 44 μm, whereby the sample object 20 and the absorption grating 4 are set at third relative positions. After moving the absorption grating 4, X-rays are applied to the sample object 20 again. Thus, a moire pattern formed when the absorption grating 4 is at the third relative positions is detected.

While the detector 5 undergoes a single detecting action, the sample object 20 and the absorption grating 4 are moved among the first, second, and third relative positions. Therefore, the moire patterns formed by the absorption grating 4 moved among the three positions are combined into one result of detection.

When the absorption grating 4 is moved, any irregularly arranged regions of the absorption grating 4 are moved correspondingly.

That is, the irregularly arranged regions are moved in a single detecting action. Therefore, a moire pattern that cannot be detected in the related art in which the absorption grating 4 is not moved can be detected. However, the contrast of the moire pattern is reduced more in portions where the transmission of X-rays is disturbed by the irregularly arranged regions when the sample object 20 and the absorption grating 4 are at the first, second, and third relative positions than in the other portions. Therefore, the amount of application of X-rays and the detection time are set so that phase information on the sample object 20 can be retrieved from such portions.

Since phase retrieval is performed through Fourier transformation by using one result obtained in a single detecting action, phase information on any missing parts that may occur in a case where imaging is performed without moving the absorption grating 4 can be acquired.

Second Exemplary Embodiment

Moving Diffraction Grating and Absorption Grating with Relative Positions Thereof Fixed A second exemplary embodiment of the present invention concerns an exemplary X-ray imaging apparatus in which the relative positions of the sample object 20 and the absorption grating 4 are changed by moving the diffraction grating 3 and the absorption grating 4 with the relative positions of the diffraction grating 3 and the absorption grating 4 being fixed. The apparatus according to the second exemplary embodiment is the same as that according to the first exemplary embodiment except that the diffraction grating 3 and the absorption grating 4 are fixed such that the relative positions thereof do not change, that the actuator 7 moves both the absorption grating 4 and the diffraction grating 3, and the lengths of movement of the diffraction grating 3 and the absorption grating 4. In the second exemplary embodiment, the absorption grating 4 and the diffraction grating 3 are moved twice in the periodic direction of the absorption grating 4 by 200 μm at a time. That is, the second relative positions of the sample object 20 and the absorption grating 4 correspond to positions of the sample object 20 and the absorption grating 4 that have been moved relative to each other from the respective first relative positions by 200 μm in the periodic direction of the absorption grating 4, and the third relative positions of the sample object 20 and the absorption grating 4 correspond to positions of the sample object 20 and the absorption grating 4 that have been moved relative to each other from the respective second relative positions by 200 μm in the periodic direction of the absorption grating 4.

As in the first exemplary embodiment, the detector 5 detects a moire pattern formed with the relative movements of the sample object 20 and the absorption grating 4 realized by the movement of the absorption grating 4, and the arithmetic unit 9 performs phase retrieval on the basis of the result of detection. Thus, phase information the same as that acquired in the first exemplary embodiment is acquired.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-265894 filed Dec. 5, 2011, which is hereby incorporated by reference herein in its entirety.

What is claimed is:

1. An X-ray imaging apparatus comprising:
   a diffraction grating that forms an interference pattern by diffracting X-rays emitted from an X-ray source;
   an absorption grating that shields a portion of the interference pattern;
   a detector that detects the X-rays emitted from the absorption grating; and
   a moving unit that changes relative positions of a sample object and the absorption grating,
   wherein the sample object is positioned between the X-ray source and the diffraction grating or between the diffraction grating and the absorption grating,
   wherein the moving unit changes the relative positions of the sample object and the absorption grating from first relative positions to second relative positions,
   wherein the detector detects the X-rays at least when the sample object and the absorption grating are at the first relative positions and when the sample object and the absorption grating are at the second relative positions, and
   wherein the second relative positions correspond to relative positions of the sample object and the absorption grating in at least one of a state where the sample object and the absorption grating have been moved relative to each other from the first relative positions in a periodic direction of the absorption grating by a length corresponding to an integral multiple of a period of the absorption grating and a state where the sample object and the absorption grating have been rotated relative to each other from the first relative positions in a plane perpendicular to an X-ray axis by an angle corresponding to an integral multiple of 180/n degrees, where n denotes the number of periodic directions of the absorption grating.

2. The X-ray imaging apparatus according to claim 1,
   wherein the second relative positions correspond to positions of the sample object and the absorption grating in the state where the sample object and the absorption grating have been moved relative to each other from the first relative positions in the periodic direction of the absorption grating by a length corresponding to an integral multiple of the period of the absorption grating,
   wherein the absorption grating has a structure in which shielding portions that block the X-rays and transmissive portions that transmit the X-rays are arranged, and
   wherein, in a periodic direction of the absorption grating, a distance of relative movement from the first relative positions to the second relative positions is shorter than a length of an area in which the shielding portions and the transmissive portions of the absorption grating are provided.

3. The X-ray imaging apparatus according to claim 1,
   wherein the absorption grating has a structure in which shielding portions that block the X-rays and transmissive portions that transmit the X-rays are arranged,
   wherein the absorption grating includes an irregularly arranged region in which the shielding portions and the transmissive portions are irregularly arranged,
   wherein the second relative positions correspond to positions of the sample object and the absorption grating in the state where the sample object and the absorption grating have been moved relative to each other from the first relative positions in the periodic direction of the absorption grating by a length corresponding to an integral multiple of the period of the absorption grating, and
   wherein, in a periodic direction of the absorption grating, a distance of relative movement from the first relative positions to the second relative positions is longer than a length of the irregularly arranged region.

4. The X-ray imaging apparatus according to claim 1,
   wherein the second relative positions correspond to positions of the sample object and the absorption grating in a state where the sample object and the absorption grating have been moved relative to each other from the first relative positions in the periodic direction of the absorption grating by a length corresponding to an integral multiple of the period of the absorption grating and have been rotated relative to each other in the plane perpendicular to the X-ray axis by an angle corresponding to an integral multiple of 180/n degrees.

5. The X-ray imaging apparatus according to claim 1,
   wherein the absorption grating has a structure in which shielding portions that block the X-rays and transmissive portions that transmit the X-rays are arranged,
   wherein the absorption grating includes an irregularly arranged region in which the shielding portions and the transmissive portions are irregularly arranged,
   wherein the second relative positions correspond to positions of the sample object and the absorption grating in the state where the sample object and the absorption grating have been rotated relative to each other from the first relative positions in the plane perpendicular to the X-ray axis by an angle corresponding to an integral multiple of 180/n degrees, and
   wherein the moving unit rotates the sample object and the absorption grating relative to each other about any position that is free of the irregularly arranged region.

6. The X-ray imaging apparatus according to claim 1, further comprising an arithmetic unit that calculates phase information on the sample object on the basis of a result of detection by the detector.

7. The X-ray imaging apparatus according to claim 6,
   wherein the detector performs detection in each of a state where the absorption grating is at the first relative position and a state where the absorption grating is at the second relative position, and
   wherein the arithmetic unit calculates the phase information on the sample object by using a result of detection of the X-rays obtained when the absorption grating is at the first relative position and a result of detection of the X-rays obtained when the absorption grating is at the second relative position.

8. The X-ray imaging apparatus according to claim 7, wherein the arithmetic unit calculates the phase information on the sample object by performing phase retrieval after combining the result of detection obtained when the absorption grating is at the first relative position and the result of detection obtained when the absorption grating is at the second relative position.

9. The X-ray imaging apparatus according to claim 1, wherein the relative positions of the diffraction grating and the absorption grating are fixed.

10. The X-ray imaging apparatus according to claim 1, wherein while the relative positions of the absorption grating and the sample object are changed from the first relative positions to the second relative positions, the application of the X-rays to the sample object is stopped.

11. The X-ray imaging apparatus according to claim 1, wherein the detector detects the X-rays obtained when the absorption grating is at the first relative position and the X-rays obtained when the absorption grating is at the second relative position in a single detecting action.

12. An X-ray imaging method comprising:
forming an interference pattern by diffracting X-rays emitted from an X-ray source;
shielding a portion of the interference pattern with an absorption grating;
detecting X-rays emitted from the absorption grating when a sample object and the absorption grating are at first relative positions;
detecting X-rays emitted from the absorption grating when the sample object and the absorption grating are at second relative positions; and
changing positions of the sample object and the absorption grating from the first relative positions to the second relative positions,
wherein the sample object is positioned between the X-ray source and the absorption grating, and
wherein the second relative positions correspond to positions of the sample object and the absorption grating in a state where the sample object and the absorption grating have been moved relative to each other from the first relative positions in a periodic direction of the absorption grating by a length corresponding to an integral multiple of a period of the absorption grating, or positions of the sample object and the absorption grating in a state where the sample object and the absorption grating have been rotated relative to each other from the first relative positions in a plane perpendicular to an X-ray axis by an angle corresponding to an integral multiple of 180/n degrees, where n denotes the number of periodic directions of the absorption grating.

13. The X-ray imaging method according to claim 12, wherein the detection of X-rays emitted from the absorption grating when the sample object and the absorption grating are at the first relative positions and the detection of X-rays emitted from the absorption grating when the sample object and the absorption grating are at the second relative positions are performed in a single detecting action of a detector.

14. A non-transitory computer readable medium storing a computer-executable program, the program causing a computer to perform a method comprising:
forming an interference pattern by diffracting X-rays emitted from an X-ray source;
shielding a portion of the interference pattern with an absorption grating;
detecting X-rays emitted from the absorption grating when a sample object and the absorption grating are at first relative positions;
detecting X-rays emitted from the absorption grating when the sample object and the absorption grating are at second relative positions; and
changing positions of the sample object and the absorption grating from the first relative positions to the second relative positions,
wherein the sample object is positioned between the X-ray source and the absorption grating, and
wherein the second relative positions correspond to positions of the sample object and the absorption grating in a state where the sample object and the absorption grating have been moved relative to each other from the first relative positions in a periodic direction of the absorption grating by a length corresponding to an integral multiple of a period of the absorption grating, or positions of the sample object and the absorption grating in a state where the sample object and the absorption grating have been rotated relative to each other from the first relative positions in a plane perpendicular to an X-ray axis by an angle corresponding to an integral multiple of 180/n degrees, where n denotes the number of periodic directions of the absorption grating.

15. The computer program according to claim 14, wherein the detection of X-rays emitted from the absorption grating when the sample object and the absorption grating are at the first relative positions and the detection of X-rays emitted from the absorption grating when the sample object and the absorption grating are at the second relative positions are performed in a single detecting action of a detector.

* * * * *